(12) United States Patent
Maliga et al.

(10) Patent No.: US 6,376,744 B1
(45) Date of Patent: Apr. 23, 2002

(54) **PLASTID TRANSFORMATION IN *ARABIDOPSIS THALIANA***

(75) Inventors: Pal Maliga, East Brunswick, NJ (US); Samir Sikdar, Calcutta; Siva Vanga Reddy, New Delhi, both of (IN)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/142,114
(22) PCT Filed: Mar. 6, 1997
(86) PCT No.: PCT/US97/03444
§ 371 Date: Feb. 5, 1999
§ 102(e) Date: Feb. 5, 1999
(87) PCT Pub. No.: WO97/32977
PCT Pub. Date: Sep. 12, 1997

Related U.S. Application Data

(60) Provisional application No. 60/012,916, filed on Mar. 6, 1996.
(51) Int. Cl.$^7$ .................. C12N 15/82; C12N 15/31; C12N 5/04; A01H 4/00; A01H 5/00
(52) U.S. Cl. ............ 800/278; 800/292; 800/293; 800/288; 800/300; 800/306; 435/320.1; 435/418; 435/419; 435/430.1; 435/431; 435/468; 435/470
(58) Field of Search .............. 435/468, 430.1, 435/431, 470, 418, 419, 320.1; 800/278, 288, 300, 306, 292, 293

(56) References Cited

U.S. PATENT DOCUMENTS

| | | | |
|---|---|---|---|
| 5,451,513 A | 9/1995 | Maliga et al. | 435/172.3 |
| 5,545,818 A | 8/1996 | McBride et al. | 800/205 |
| 5,576,198 A | 11/1996 | McBride et al. | 435/91.3 |
| 5,877,402 A | 3/1999 | Maliga et al. | 800/205 |

FOREIGN PATENT DOCUMENTS

| | | |
|---|---|---|
| EP | 0142924 A2 | 5/1985 |
| EP | 0589841 A2 | 3/1994 |

OTHER PUBLICATIONS

A Dictionary of Science, Oxford Univ. Press, Market House Books Ltd, "Plastid" entry, 1999.*
Heifetz et al. Curr. Opinion Plant Biology 4:157–161, 2001.*
Svab et al. Proc. Natl. Acad. Sci. USA 87:8526–8530, Nov. 1990.*
Iida et al. Theor. Appl. Genet. 80:813–816, 1990.*
Lloyd et al. Science 234:464–466, Oct. 1986.*
Palmer et al. pp. 37–62 In: Arabidopsis, Meyerowitz et al., eds, Cold Spring Harbor Lab. Press, 1994.*
Jeffrey M. Staub, et al. Long Regions of Homologous DNA are Incorporated into the Tobacco Plastid Genome by Transformation. The Plant Cell. (Jan. 1992) 4:39–45.
Sumita Chaudhuri, et al. Site–Specific factor involved in the editing of the psbl mRNA in tobacco plastids. The EMBO Journal. (1995) 14, 12: 2951–2957.
Jeffrey M. Staub, et al. Expression of a chimeric uidA gene indicates that polycistronic mRNAs are efficiently translated in tobacco plastids. The Plant Journal. (1995) 7,5: 845–848.
Jeffrey M. Staub, et al. Marker rescue from the *Nicotiana tabacum* plastid genome using a plastid/*Escherichia coli* shuttle vector. Mol. Gen. Genet. (1995) 249:37–42.
H.–U. Koop Ch 9. Plastid Transformation by Polyethylene Glycol Treatment of Protoplasts and Regeneration of Transplastomic Tobacco Plants. pp. 75–82.
Oleg V. Zoubenko, et al. Efficient targeting of foreign genes into the tobacco plastid genome. Nucleic Acids Research. (1994) 22,19: 3819–3824.
Helaine Carrer, et al. Kanamycin resistance as a selectable marker for plastid transformation in tobacco. Mol. Gen Genet. (1993) 241: 49–56.
Christina M. Richards, et al. Survey of plastid RNA abundance during tomato fruit ripening: the amounts of RNA from the ORF 2280 region increase in chromoplasts. Plant Molecular Biology. (1991) 17:1179–1188.

* cited by examiner

Primary Examiner—David T. Fox
(74) Attorney, Agent, or Firm—Dann, Dorfman, Herrell and Skillman

(57) ABSTRACT

The invention provides methods and compositions for obtaining transplastomic *Arabidopsis* plants. Specifically, the method provides culturing protocols and compositions that facilitate the regeneration of transformed plants following delivery of exogenous DNA molecules.

13 Claims, 7 Drawing Sheets

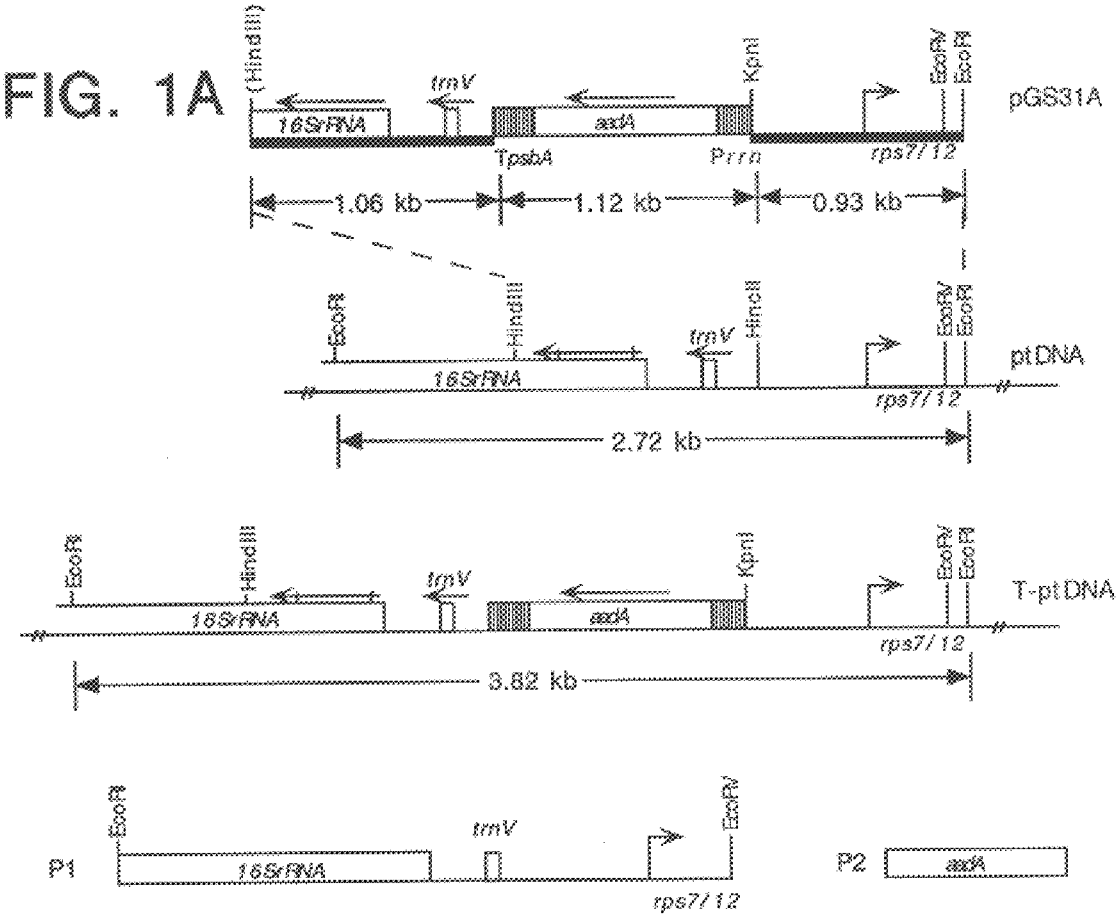
FIG. 1A
FIG. 1B
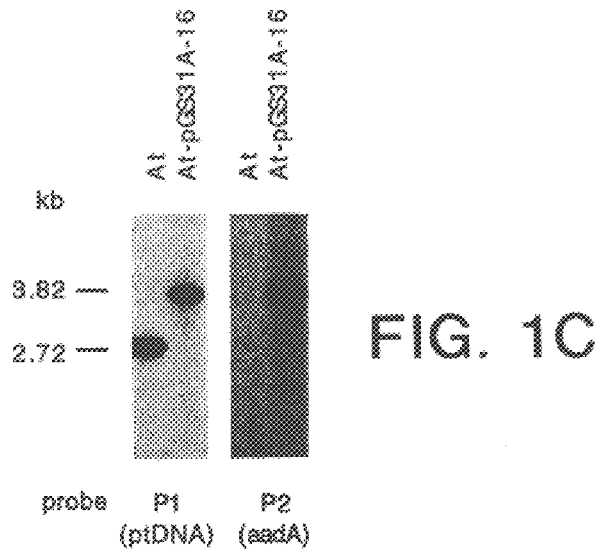
FIG. 1C

*HindIII*
```
   1 AAGCTTGGTA GTTTCCACCG CCTGTCCAGG GTTGAGCCCT GGGATTTGAC
  51 GGCGGACTTA AAAAGCCACC TACAGACGCT TTACGCCCAA TCATTCCGGA
 101 TAACGCTTGC ATCCTCTGTA TTACCGCGGC TGCTGGCACA GAGTTAGCCG
 151 ATGCTTATTC CCCAGATACC GTCATTGCTT CTTCTCTGGG AAAAGAAGTT
 201 CAGGACCCGT AGGCCTTCTA CCTCCACGCG GCATTGCTCC GTCAGGCTTT
 251 CGCCCATTGC GGAAAATTCC CCACTGCTGC CTCCCGTAGG AGTCTGGGCC
 301 GTGTCTCAGT CCCAGTGTGG CTGATCATCC TCTCGGACCA GCTACTGATC
 351 ATCGCCTTGG TAAGCTATTG CCTCACCAAC TAGCTAATCA GACGCGAGCC
 401 CCTCCTCGGG CGGATTCCTC CTTTTGCTCC TCAGCTACGG GGTATTAGCA
 451 GCCGTTTCCA GCTGTTGTTC CCCTCCCAAG GGNAGGTTCT TACGCGTTAC
 501 TCAcCNGTCC GCCACTGGAA ACACCACTTC CCGTCGACT TGCATGTGTT
 551 AAGCATGCCG CCAGCGTTCA TCCTGAGCCA GGATCGAACT CTCCATGAGA
 601 TTCATAGTTG CATTACTTAT AGCTTCCTTC TTCGTAGACA AAGCTGATTC
 651 GGAATTGTCT TTCATTCCAA GTCATAACTT GTATCCATGC GCTTCATATT
 701 CGCATGGAGT TCGCTCCCAG AAATATAGCT ACCCCTACCC CCTCACGTCA
 751 ATCCCACGAG CCTCTTATCC ATTCTTATTC GATCACAGCG AGGGAGCAAG
 801 TCAAAATAGA AAAACTCACA TTCATTGGGT TTAGGGATAA TCAGGCTCGA
 851 ACTGATGACT TCCACCACGT CAAGGTGACA CTCTACCGCT GAGTTATATC
 901 CCTTCCCCCA TCAAGAAATA GAACTGACTA ATCCTAAGTC AAAGGGTCGA
 951 GAAACTCAAG GCCACTATTC TTGAACAACT TGGATTGGAG CCGGGCTTTC
1001 CTTTCGCACT TTATACGGGT ATGAAATGAA ATAATGGAA  AAAGTTGGAT
1051 TCAATTGTCA ACTACTCCTA TCGGAAATAG GATTGACTAC GGATTCGAGC
1101 CATAGCACAT GGTTTCATAA AACCGTACGA TTCTCCCGAT CTAAATCAAG
1151 CCGGTTTTAC ATGAAGAAGA TTTGACTCGG CATGTTCTAT TCGATACGGG
1201 TAGGAGAAAC GGTATTCTTT TCTTAAACTT CAAAAAATAG AGAAATAAGA
1251 ACCAAGTCAA GATGATACGG ATTAATCCTT TATTCTTGCG CCAAAGATCT
1301 TCCTATTCCA AGGAACTGGA GTTACATCTC TTTTCCATTT CCATTCAAGA
1351 GTTCTTATGT GTTTCCACgC CCCTTTAAGA cCCCGAAAAA TCGACAAATT
1401 CCCTTTTCTT AGGACCACAT GCGAGATAAC GAAAAAAAAA AAGAGAGAAT
1451 GGTAACCCCA CGATTAACTA TTTTATTTAT GAATTTCATA GTAATAGAAA
1501 TACATGTCCT ACCGAAACAG AATTTGTAAC TTGCTATCCT ATCATCTTGC
1551 CTAGCAGGCA AAGATTTCAC TCCGCGAAAA AGATGATTCA TTCGGATCAA
1601 CATGAAAGCC CAACTACATT GCCAGAATTT ATATATTGGA AAGAGGTTTA
1651 CCTCCTTGCT TCTATGGTAC AATCCTCTTC CCGCGGAGCC TCCTTTCTTC
1701 TCGGTCCGCA GAGACAAAAT GTAGGACTGG TGCCAACAGT TAATCACGGA
1751 AGAAAGGACT CACTGCGCCA AGATCACTAA CTAATCTAAT AGAATAGAAA
1801 ATCCTAATAT AATAGAAAAG AAAAGAACTG TCTTTTCTGA TACTTATGTA
1851 TACTTTCCCC GGTTCCGTTG CTACTGCGGS TTTACGCAAT TGATCGGATC
1901 ATCTAGATAT CCCTTCAACA CAACATAGGT CGTCGAAAGG ATCTCGGAGA
1951 CCCGCCAAAG CACGAAAGCC AGAATCTTTC AGAAAATGAA TTC
```
                                                              *HincII*

*EcoRI*

FIG. 5 pGS31A derived by inserting Prrn::aadA::Tpsba as Ecl136II/BspHI
blunt from pZS179 XbaI site filled in
pGS31A.seq Length: 1143 March 6, 1997 19:58 Type: N Check: 380

>SEQED (include) reverse of: PrrnaadATpsbA.seq
check: 5330 from: 10 to 1152>

```
   1  CATGAATAAA TGCAAGAAAA TAACCTCTCC TTCTTTTTCT ATAATGTAAA

51  CAAAAAGTC  TATGTAAGTA  AAATACTAGT AAATAAATAA AAAGAAAAAA

101  AGAAAGGAGC AATAGCACCC TCTTGATAGA ACAAGAAAAT GATTATTGCT

151  CCTTTCTTTT CAAAACCTCC TATAGACTAG GCCAGGATCg ctctagct
```
<SEQED
(include) reverse of: pOVZ44a.seq check: 1487 from: 1954 to: 2898<

```
                                                      ctagctag
 201  acattatttg ccgactacct tggtgatctc gcctttcacg tagtggacaa 251  attcttccaa ctgatctgcg cgcgaggcca agcgatcttc ttcttgtcca 301  agataagcct gtctagcttc aagtatgacg ggctgatact gggccggcag 351  gcgctccatt gcccagtcgg cagcgacatc cttcggcgcg attttgccgg 401  ttactgcgct gtaccaaatg cgggacaacg taagcactac atttcgctca 451  tcgccagccc agtcgggcgg cgagttccat agcgttaagg tttcatttag 501  cgcctcaaat agatcctgtt caagaaccgg atcaaagagt tcctccgccg 551  ctggacctac caaggcaacg ctatgttctc ttgcttttgt cagcaagata 601  gccagatcaa tgtcgatcgt ggctggctcg aagatacctg caagaatgtc 651  attgcgctgc cattctccaa attgcagttc gcgcttagct ggataacgcc 701  acggaatgat gtcgtcgtgc acaacaatgg tgacttctac agcgcggaga 751  atctcgctct ctccagggga agccgaagtt tccaaaggt  cgttgatcaa 801  agctcgccgc gttgtttcat caagccttac ggtcaccgta accagcaaat 851  caatatcact gtgtggcttc aggccgccat ccactgcgga gccgtacaaa 901  tgtacggcca gcaacgtcgg ttcgagatgg cgctcgatga cgccaactac 951  ctctgatagt tgagtcgata cttcggcgat caccgcttcT GCcatAAATC

1001  CCTCCCTACA ACTGTATCCA AGCGCTTCGT ATTCGCCCGG AGTTCGCTCC

1051  CAGAAATATA GCCATCCCTG CCCCCTCACG TCAATCCCAC GAGCCTCTTA

1101  TCCATTCTCA TTGAACGACG GCGGGGGAGC tttg
```
Prrn::aadA::TpsbA

<SEQED (include)
reverse of: pOVZ44a.seq check: 1487 from: 1954 to:
2898> ggtacc gag

FIG. 6

```
                    | Included
        1  gaattcgagc tcggtaccca aaGCTCCCCC GCCGTCGTTC AATGAGAATG
       51  GATAAGAGGC TCGTGGGATT GACGTGAGGG GGCAGGGATG GCTATATTTC
      101  TGGGAGCGAA CTCCGGGCGA ATACGAAGCG CTTGGATACA GTTGTAGGGA
      151  GGGATTTATG TCACCACAAA CAGAGGGGAT TGAACAAGAT GGATTGCACG
      201  CAGGTTCTCC GGCCGCTTGG GTGGAGAGGC TATTCGGCTA TGACTGGGCA
      251  CAACAGACAA TCGGCTGCTC TGATGCCGCC GTGTTCCGGC TGTCAGCGCA
      301  GGGGCGCCCG GTTCTTTTTG TCAAGACCGA CCTGTCCGGT GCCCTGAATG
      351  AACTCCAGGA CGAGGCAGCG CGGCTATCGT GGCTGGCCAC GACGGGCGTT
      401  CCTTGCGCAG CTGTGCTCGA CGTTGTCACT GAAGCGGGAA GGGACTGGCT
      451  GCTATTGGGC GAAGTGCCGG GGCAGGATCT CCTGTCATCT CACCTTGCTC
      501  CTGCCGAGAA AGTATCCATC ATGGCTGATG CAATGCGGCG GCTGCATACG
      551  CTTGATCCGG CTACCTGCCC ATTCGACCAC CAAGCGAAAC ATCGCATCGA
      601  GCGAGCACGT ACTCGGATGG AAGCCGGTCT TGTCGATCAG GATGATCTGG
      651  ACGAAGAGCA TCAGGGGCTC GCGCCAGCCG AACTGTTCGC CAGGCTCAAG
      701  GCGCGCATGC CCGACGGCGA GGATCTCGTC GTGACACATG GCGATGCCTG
      751  CTTGCCGAAT ATCATGGTGG AAAATGGCCG CTTTTCTGGA TTCATCGACT
      801  GTGGCCGGCT GGGTGTGGCG GACCGCTATC AGGACATAGC GTTGGCTACC
      851  CGTGATATTG CTGAAGAGCT TGGCGGCGAA TGGGCTGACC GCTTCCTCGT
      901  GCTTTACGGT ATCGCCGCTC CCGATTCGCA GCGCATCGCC TTCTATCGCC
      951  TTCTTGACGA GTTCTTCTGA GCGGGACTCT GGGGTTCGGA TCGATCCtct
     1001  aggGCGATCC TGGCCTAGTC TATAGGAGGT TTTGAAAAGA AAGGAGCAAT
     1051  AATCATTTTC TTGTTCTATC AAGAGGGTGC TATTGCTCCT TTCTTTTTTT
     1101  CTTTTTATTT ATTTACTAGT ATTTTACTTA CATAGACTTT TTTGTTTACA
     1151  TTATAGAAAA AGAAGGAGAG GTTATTTTCT TGCATTTATT CATGATTGAG
     1201  TATTCTATTT TGATTTTGTA TTTGTTTAAA TTGTGAAATA GAACTTGTTT
     1251  CTCTTCTTGC TAATGTTACT ATATCTTTTT GATTTTTTTT TTCCAAAAAA
     1301  AAAATCAAAT TTTGACTTCT TCTTATCTCT TATCTTTGAA TATCTCTTAT
     1351  CTTTGAAATA ATAATATCAT TGAAATAAGA AAGAAGAGCT ATATTCGAcc
     1401  tgcaggcatg caagctt                              Included
```

| HindHIII-GTC | cggta-kan-TTCGAcc | AAC-EcoRI |
| pGS7 | | pGS7 |

FIG. 7

PLASTID TRANSFORMATION IN *ARABIDOPSIS THALIANA*

CROSS-REFERENCE TO RELATED APPLICATIONS

The present application claims priority under 35 U.S.C. §371 to international application PCT/US97/03444, filed on Mar. 6, 1997, and published as WO97/32977, which in turn claims priority from U.S. Application No. 60/012,916, filed on Mar. 6, 1996.

Pursuant to 35 U.S.C. Section 202(c), it is acknowledged that the United States government has certain rights in the invention describe herein, which was made in part with funds from the National Science Foundation Grant Number, MCB 93-05037.

FIELD OF THE INVENTION

The present invention relates to the field of transgenic plants. Specifically, the invention provides compositions and methods for the transformation of plastids in plants from the Cruciferae family.

BACKGROUND OP THE INVENTION

Several publications are parenthetically referenced in this application in order to more fully describe the state of the art to which this invention pertains. Full citations for these references are found at the end of the specification. The disclosure of each of these publications is incorporated by reference in the present specification as though set forth herein in full.

The plastid genome of higher plants is a circular double-stranded DNA molecule of 120–160 kb which may be present in 1,900–50,000 copies per leaf cell (Palmer, 1991; Bendich, 1987). Stable transformation of the tobacco plastid genome (plastome) has been achieved through the following steps: (i) introduction of transforming DNA, encoding antibiotic resistance, by the biolistic process (Svab et al. 1990a; Svab and Maliga 1993) or PEG treatment (Golds et al. 1993; O'Neill et al., 1993), (ii) integration of the transforming DNA by two homologous recombination events and (iii) selective elimination of the wild-type genome copies during repeated cell divisions on a selective medium. Spectinomycin resistance has been used as a selective marker encoded either in mutant plastid 16S ribosomal RNA genes (Svab et al. 1990a; Staub and Maliga 1992; Golds et al. 1993), or conferred by the expression of an engineered bacterial aadA gene (Svab and Maliga 1993). Vectors which utilize aadA as a selectable marker gene and target the insertion of chimeric genes into the repeated region of tobacco plastid genome are available (Zoubenko et al., 1994). Selection of plastid transformants by kanamycin resistance, based on the expression of neomycin phosphotransferase (kan gene), is more difficult but also feasible (Carrer et al., 1993; Carrer and Maliga, 1995).

To date, stable plastid transformation in higher plants has been reported in tobacco only (reviewed in Maliga, 1993; Maliga et al., 1993). Transplastomic plants from other agriculturally and pharmaceutically important species are highly desirable. Expression of foreign genes of interest in the plastids of higher plants in the family Cruciferae provides several advantages over nuclear expression of foreign genes. These are 1) expression of exogenous DNA sequences in plastids eliminates the possibility of pollen transmission of transforming DNA; 2) high levels of protein expression are attainable; 3) the simultaneous expression of multiple genes as a polycistronic unit is feasible and 4) positional effects and gene silencing which may result following nuclear transformation are also eliminated.

SUMMARY OF THE INVENTION

The present invention provides improved methods for the generation of stably transformed, transplastomic plants. In one embodiment of the invention, cotyledon cells are cultured in high auxin liquid medium for a sufficient time period to stimulate uniform cell division. Initial culture is at a high density (50–200 cotyledons/20 ml). The cotyledons are then transferred to agar-solidified medium for delivery of exogenous, transforming DNA. Following delivery of transforming DNA, the cotyledons are transferred at a lower density (25–30/50 ml) to a medium containing high cytokinin level and the selection agent to facilitate selection of transformants and plant regeneration. Presence of the exogenous DNA in the plastid genome is then confirmed by Southern blot analysis or PCR.

The transforming DNA molecules of the invention have several distinct features. These are 1) targeting segments flanking the foreign gene of interest consisting of plastid DNA sequences from the plant to be transformed, thereby facilitating homologous recombination of the transforming DNA into a pre-determined region of the plastid genome; 2) a selectable marker gene disposed within the targeting segment, conferring resistance to a selection agent; 3) 5' and 3' regulatory sequences derived from plastid DNA operably linked to sequences encoding a foreign gene of interest thereby enhancing expression of the transforming DNA and stability of encoded mRNA; and 4) at least one cloning site adjacent to the selectable marker gene for insertion of the foreign gene of interest which by itself is not selectable. Since the selectable marker gene and the foreign gene of interest form a heterologous block of contiguous sequence, integration of both genes into the plasid genome is effected.

In another embodiment of the invention, leaf cells are initially treated with high auxin media, followed by transformation with the transforming DNA and culturing in the presence of high cytokinin levels and a predetermined selection agent. Cells containing transformed plastids are maintained in the presence of the selection agent facilitating the obtention of homoplasmic cells which can then be regenerated into transplastomic plants.

Thus, the present invention provides novel methods and compositions for creating transplastomic plants. The genus Arabidopsis belongs to the mustard or crucifer family (Brassicaceae or Cruciferae), a widely distributed family of approximately 340 genera and 3350 species. The family is of significant economic importance as a source of vegetable crops, oil seeds, spices and, to a lesser extent, ornamentals. Much of its agricultural importance derives from the genus Brassica. Examples for Brassica ssp. of economic importance are: *Brassica napus* (oil seed), *Brassica juncea* (oil seed), *Brassica campestris* (oil seed), *Brassica juncea* (oil seed), *Brassica oleracea* (broccoli, cauliflower, cabbage) *Brassica nigra* (black mustard) and *Brassica hirta* (white mustard).

Plastid transformation in *Arabidopsis thaliana* a model species for plant research (Meyerowitz and Sommerville, 1994) and Brassica ssp., an important agricultural crop is exemplified herein. These methods are suitable for transformation of plastids in other plants from the Cruciferae family.

BRIEF DESCRIPTION OF THE DRAWINGS

FIGS. 1A–1C are a schematic drawing illustrating the integration of aadA into the Arabidopsis plastid genome (ptDNA) after transformation with plasmid pGS31A. FIG. 1A shows a map of the transformation vector pGS31A, the ptDNA region containing the integrated spectinomcycin resistance (aadA) gene (T-ptDNA) and the cognate region of the wild-type ptDNA. 16SrDNA, rps12/7 and trnV are plastid genes (Shinozaki et al., 1986). FIG. 1B shows the regions of ptDNA contained in the P1 and P2 probes. FIG. 1C is an autoradiogram showing the results of Southern blot hybridization confirming integration of aadA in the plastid genome. The P1 targeting sequences hybridize to a 2.72-kb fragment in the wild-type (At) plants and to a larger, 3.82-kb fragment in the transplastomic line (At-pGS31A-16). Note absence of wild-type fragment in transplastomic line. The aadA probe, P2, hybridizes only to the larger transplastomic fragment.

FIG. 5 is a sequence of the targeting region of plasmid pGS7. The genes conferring resistance to kanamycin or spectinomycin will be inserted into the marked Hinc II site FIG. 6 is a sequence of the plastid targeting region of plasmid pGS31A.

FIG. 7 is the sequence of the plastid targeting region of plasmid pGS85A.

DETAILED DESCRIPTION OF THE INVENTION

Figure 2:
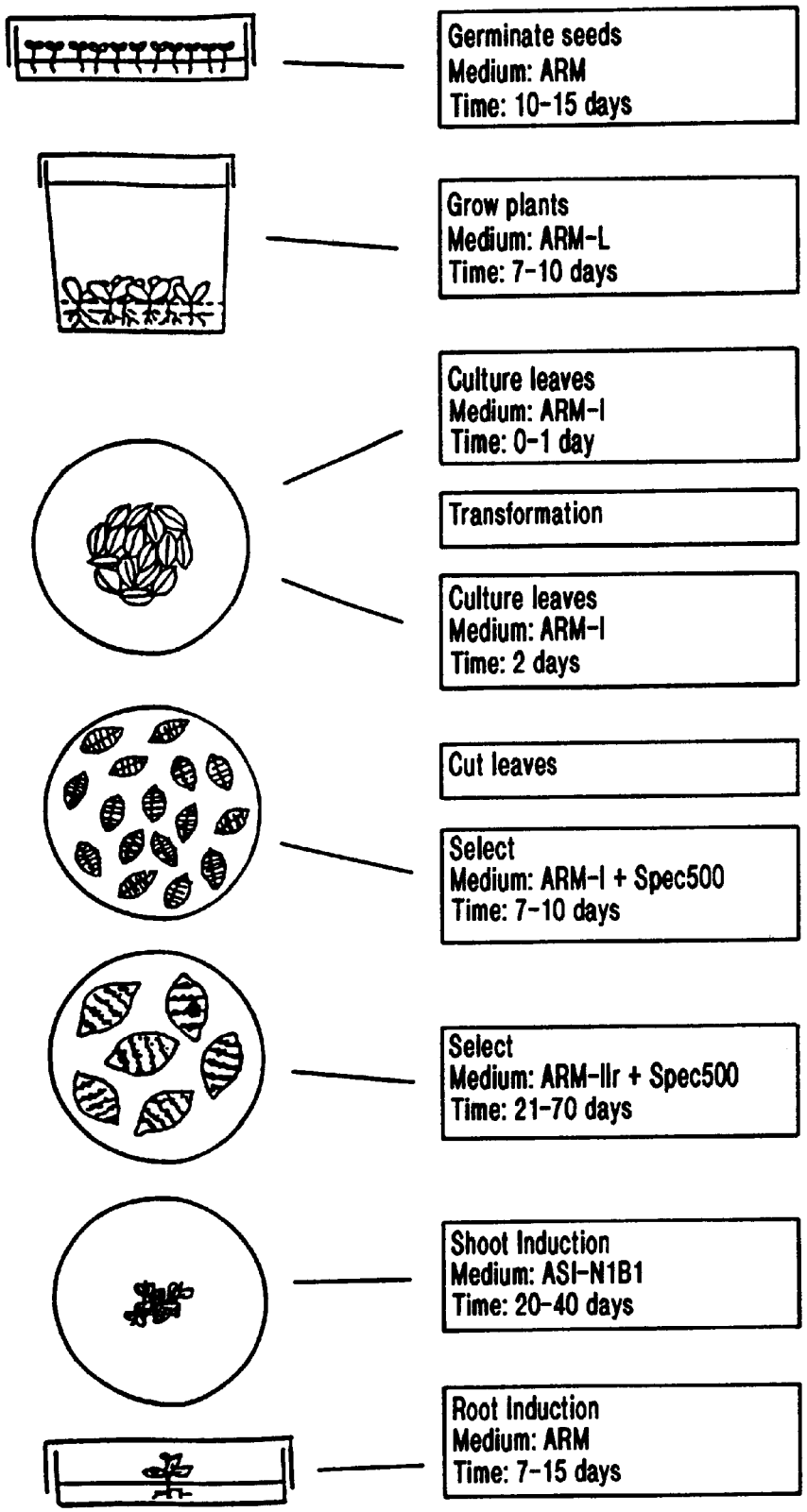
FIG. 2 is a schematic diagram of the plastid transformation protocol used for Arabidopsis leaves.

Insofar as it is known, plastid transformation has been demonstrated in tobacco only. A protocol for the transformation of plastids in *Arabidopsis thaliana* and *Brassica napus* has now been developed and the methods utilized to create these transformants are set forth below. The use of Arabidopsis and Brassica in the following examples is meant to be illustrative of the methods of the invention. The methods disclosed herein may be adapted to other plants in the Cruciferae family.

The plastids of *Arabidopsis thaliana* have been transformed following biolistic delivery of transforming DNA into leaf cells on the surface of microscopic (1 μm) tungsten particles as described below in Example I. The transforming plasmid pGS31A, used for these experiments carries a spectinomycin resistance (aadA) gene flanked by plastid DNA sequences to target its insertion between trnV and the rps 12/7 operon. Integration of aadA by two homologous recombination events via the flanking ptDNA sequences and selective amplification of the transplastomes on spectinomycin medium yielded spectinomycin resistant cell lines. Regenerated plants were homoplasmic in that the plastid genome copies had been uniformly altered by the transforming DNA. The efficiency of plastid transformation was low, two in 201 bombarded leaf samples. However, none of the 98 plants regenerated from the two lines were fertile.

These fertility problems were likely attributable to extended periods of treatment with 2,4-D, an auxin (Van der Graaff and Hooykas, 1996). It is possible that shortening exposure time to this agent may overcome the fertility problem. The relatively long growth period of *Arabidopsis thaliana* to provide a suitable source of leaves for transformation also makes leaves a less desirable tissue source.

Cotyledons and leaves each contain an abundant number of plastid genome copies per cell. Additionally, cotyledons provide a more available tissue source. Accordingly, cotyledon cells have been utilized as recipients for transforming DNA as set forth in Example II below. Cotyledon cells are preferred over leaf cells for practicing the methods of the present invention due to the relatively short (7 days) culturing period to prepare the cells for bombardment with transforming DNA. Another advantage to using cotyledon cells as the target cell is the reported regeneration of fertile Arabidopsis plants from immature cotyledons in the absence of 2,4-D (Patton and Meinke, 1988). In addition, protocols have been described for the regeneration of fertile Arabidopsis plants from leaf explants, also in the absence of 2,4-D (Lloyd et al., 1986; Van der Graaff and Hooykas, 1996).

As described in Example III, *Arabidopsis thaliana* and *Brassica napus* belong to the same family, Cruciferae, and therefore the plastid genomes share a high degree of homology and are essentially identical (Palmer et al., 1994). Accordingly, plastid transformation vectors and expression cassettes developed for Arabidopsis can be used for plastid transformation and expression of foreign genes in Brassica species without modification.

The following definitions are provided to facilitate an understanding of the present invention:

Heteroplasmic: refers to the presence of a mixed population of different plastid genomes within a single plastid or in a population of plastids contained in plant cells or tissues.

Homoplasmic: refers to a pure population of plastid genomes, either within a plastid or within a population contained in plant cells and tissues. Homoplasmic plastids, cells or tissues are genetically stable because they contain only one type of plastid genome. Hence, they remain homoplasmic even after the selection pressure has been removed, and selfed progeny are also homoplasmic. For purposes of the present invention, heteroplasmic populations of genomes that are functionally homoplasmic (i.e., contain only minor populations of wild-type DNA or transformed genomes with sequence variations) may be referred to herein as "functionally homoplasmic" or "substantially homoplasmic." These types of cells or tissues can be readily purified to homoplasmy by continued selection on the non-lethal selection medium. Most seed progeny of such plants are homoplasmic in the absence of selection pressure, due to random sorting of plastid genomes.

Plastome: the genome of a plastid.

Transplastome: a transformed plastid genome.

Transformation of plastids: stable integration of transforming DNA into the plastid genome that is transmitted to the seed progeny of plants containing the transformed plastids.

Selectable marker: the term "selectable marker" refers to a phenotype that identifies a successfully transformed organelle, cell or tissue, when a gene or allele encoding the selectable marker is included in the foreign DNA used for transformation.

Transforming DNA: refers to homologous DNA, or heterologous DNA flanked by homologous DNA, which when introduced into plastids replaces part of the plastid genome by homologous recombination.

Targeting segment: refers to those homogologous flanking regions which facilitate homologous recombination between foreign DNA and the plastid genome.

Translationally fused: refers to two coding DNA segments within a construct derived from different sources spliced together in a construct such that a chimeric protein is expressed.

High auxin culture medium: plant tissue culture medium which contains auxin only, or a combination of high concentration of auxin and very low concentrations of cytokinins. The response of a plant cell to an auxin is specific for a given taxonomic group. When different auxins are applied in combination, their effects may not be additive. Furthermore, the tissue response to auxin may be modified by cytokinins. Accordingly, the type and concentration of auxin used should be determined empirically for the species to be transformed. A preferred example of a high auxin medium for use in the present invention is C1 medium, containing 1 mg/ml of the auxin 1-naphthaleneacetic acid (NAA) and a low concentration (0.2 mg/ml) of the cytokinin 6-benzylaminopurine (BAP). Other, auxins, such as indole-3-acetic acid (IAA) and dichloro-phenoxyaceticacid (2,4-D) may also be used to stimulate uniform cell division.

High cytokinin culture medium: Like the response of plant cells to high auxin media, the response of plant cells to high cytokinin media is taxonomic group specific. An example of a preferred high cytokinin medium for use in the present invention is C medium, containing 1 mg/L of BAP, 2 mg/L of 2iP, (6-(gamma, gamma-Dimethylallyamino) purine or IPA, N6-(Isopentenyl) adenin) and a low concentration of the auxin NAA (0.1 mg/L). Other cytokinins which may be used include 6-furfurylaminopurine (KIN or kinetin).

The detailed description provided in the following examples relates to preferred methods for making and using the DNA constructs of the present invention and for practicing the methods of the invention. Any molecular cloning and recombinant DNA techniques not specifically described are carried out by standard methods, as generally set forth, for example in Sambrook et al., "DNA Cloning, A Laboratory Manual," Cold Spring Harbor Laboratory, 1989 or Ausubel et al. eds. in "Current Protocols in Molecular Biology", John Wiley and Sons, 1995.

The following examples are provided to more fully describe the instant invention. They are not intended to limit the scope of the invention in any way.

EXAMPLE I

Plastid Transformation in Arabidopsis Leaves by Selection for Spectinomycin Resistance The following materials and protocols enable the practice of the methods of Example I. A schematic diagram of the methods utilized is provided in FIG. 2.

Plant Material

As the recipient for transformation, the Arabidopsis ecotype RLD was used. This ecotype has been reported to regenerate readily in culture (Marton and Browse, 1991).

Construction of Vector pGS31A

The Arabidopsis plastid transformation vector pGS31A is shown in FIG. 1. The immediate progenitor of pGS31A is plasmid pGS7, a pBluescript KS(+) phagemid vector (Stratagene) derivative. Plasmid pGS7 carries a 2-kb HindIII-EcoRI Arabidopsis ptDNA fragment containing the 5'-end of the 16S rRNA gene, trnV and part of the rps12/7 operon. During construction of the pGS7 plasmid the HindIII site has been removed by digestion with HindIII (site in 16SrDNA) and KpnI (in vector, treated with the T4 DNA polymerse to remove the single-stranded overhangs) and ligating the blunt ends. Vector pGS31A carries the selectable spectinomycin resistance gene, (Prrn::aadA::TpsbA) present in plasmid pZS197 (Svab and Maliga, 1993). The aadA coding region is transcribed from a synthetic promoter consisting of the promoter of the tobacco rRNA operon fused with a synthetic ribosome binding site (Prrn). The aadA mRNA is stabilized by transcriptionally fusing sequences downstream of the coding region with the 3'-untranslated region of the tobacco plastid psbA gene (TpsbA). The gene in pGS31A derives from a modified progenitor of pZS197 in which the XbaI site between aadA and TpsbA was removed by blunting. Plasmid pGS31A was obtained by excising the chimeric aadA gene with Ecl136II (an isochisomer of SacI, yields blunt ends) and BspHI (single-stranded overhang filled in to obtain blunt ends) for ligation into the unique HincII site of plasmid pGS7 between trnV and the rps12/7 operon.

Tissue Culture Media

The tissue culture protocols were adopted from Marton and Browse (1991) and Czako et al. (1993). The Arabidopsis tissue culture media (ARM) are derivatives of the Murashige & Skoog (1962) MS medium. ARM medium: MS salts, 3% sucrose, 0.8% TC agar, 2 ml/L of the vitamin solution (100 mg myo-inositol, 5 mg vitamin B1, 0.5 mg vitamin B6, 0.5 mg nicotinic acid, 1 mg glycine and 0.05 mg biotin per ml). ARMI medium: ARM medium containing 3 mg indoleacetic acid (IAA), 0.15 mg 2,4-dichlorophenoxyacetic acid (2,4-D), 0.6 mg benzyladenine (BA) and 0.3 mg isopentenyladenine (IPA) per liter. ARMIIr medium: ARM medium supplemented with 0.2 mg/L naphthaleneacetic acid (NAA) and 0.4 mg/L IPA. Arabidopsis shoot induction (ASI-N1B1) medium: ARM medium supplemented with 1 mg/L NAA and 1 mg/L BAP. The Arabidopsis shoots were rooted on ARM medium. Arabidopsis seed culture (ARM5) medium: ARM medium supplemented with 5% sucrose. The stocks of plant hormones were filter sterilized, and added to media cooled to 45° C. after autoclaving.

Selective media contained 500 mg/L spectinomycin HCl and/or streptomycin sulfate. The antibiotics (filter sterilized) were added to media cooled to 45° C. after autoclaving.

Cultivation of Arabidopsis Plants in Sterile Culture

For surface sterilization, seeds (25 mg) were treated with 1 ml of commercial bleach (5.25% sodium hypochlorite) in an Eppendorf tube for 5–7 minutes with occasional vortexing. The seeds along with the bleach were poured into a 15 ml conical centrifuge tube containing 10 ml 90% ethanol and incubated for 5–7 minutes. The ethanol-bleach mix was decanted, and the seeds were washed 4 times with 10 ml autoclaved deionized water and finally resuspended in sterile water (approximately 150 seeds/ml). The resulting seed suspension (2 ml) was poured into 10 cm deep (10 mm high) petri dishes containing 50 ml ARM5 medium. The seeds were spread evenly by swirling the suspension. The water was then removed from the plates by pipetting. The seeds germinated after a 10–15 day incubation at 24° C. during which the plates were illuminated for 8 hours using cool-white fluorescent tubes (2000 lux).

To grow plants with larger leaves, seedlings were individually transferred to ARM5 plates (10 plants per 10 cm petri dish) and illuminated for 8 hours with cool-white fluorescent bulbs (lux; 21° C. day and 18° C. night temperature). The thick, dark green leaves, 1 cm to 2 cm in size, were harvested for bombardment after 5–6 weeks.

Transformation and Selection of Spectinomycin Resistant Lines

Leaves (approximately 1.5 to 30 mm in length) for plastid transformation were harvested from aseptically grown plants. To cover a circular area 4 to 5 cm in diameter, 12 to 18 leaves were placed on agar-solidified ARMI medium. The pGS31A vector DNA was introduced into leaf chloroplasts by the biolistic process, on the surface of microscopic (1 μm) tungsten particles using a helium-driven PDS1000 biolistic gun. Fresh leaves were bombarded at 450 psi (target placed at 9 cm from rupture disk; position No. 3 from top in the biolistic gun). Leaves cultured for 4 days on ARMI medium were bombarded at 1100 psi (target placed at 12 cm from rupture disk; position No. 4 from top in the biolistic gun).

Leaf bombardment was performed in ARMI medium. Following bombardment, the leaves were incubated for two additional days in ARMI medium. After this time period, the leaves were stamped with a stack of razor blades to create a series of parallel incisions 1 mm apart. It has been observed previously that mechanical wounding is essential to induce uniform callus formation in the leaf blades. The stamped leaves were transferred onto the same medium (ARMI) containing spectinomycin (500 mg/ml) to facilitate preferential replication of plastids containing transformed ptDNA copies. The ARMI medium induces division of the leaf cells and formation of colorless, embryogenic callus. After 7–10 day selection on ARMI medium, spectinomycin selection was continued on the ARMIIr medium which normally induces greening. Since spectinomycin prevents greening of wild-type cells, only spectinomycin-resistant cells formed green calli. Visible green cell clusters on the selective ARMIIr medium appeared within 21 to 70 days.

In 201 bombarded samples 19 spectinomycin-resistant lines were obtained. Plant regeneration was attempted in 14 spectinomycin-resistant lines, and succeeded in 10 of them. Shoots from the green calli regenerated on the ASI-N1B1 medium, and were rooted on ARM medium.

Table 1 sets forth the recovery of spectinomycin resistant cell lines after biolistic delivery of plasmid pGS31A.

TABLE 1

Recovery of spectinomcyin resistant lines after bombardment of A. thaliana with plasmid pGS31A

| DNA[1] | Number of Samples | psi[2] | Number of Spc[r] Plant | Transgenic pt | Nucleus | Spont. mutant. |
|---|---|---|---|---|---|---|
| N/A | 100 | | 1 | 0 | | 1 |
| pGS31A | 40 | 1100 | 8 | 6 | 1 | 7 | 0 |
| pSG31A | 151 | 450 | 11 | 8 | 1 | 10 | 0 |

[1]The control plates were not bombarded.
[2]psi = pounds per square inch, the value of repture disk.

Southern Hybridization Analysis of Total Cellular DNA to Verify Plastid Transformation Spectinomycin resistance may be due to expression of aadA in plastids (Svab and Maliga, 1993), expression of aadA in the nucleus (Svab et al., 1990b), or spontaneous mutation (Fromm et al., 1987; Svab and Maliga, 1991). Southern hybridization was performed to identify plastid transformants in the spectinomycin resistant lines isolated. Total cellular DNA was isolated according to Mettler (1987). Restriction enzyme-digested DNA was electrophoresed in 0.7% agarose gels and transferred to nylon membrane (Amersham) using the PosiBlot transfer apparatus (Stratagene). Blots were probed by using Rapid Hybridization Buffer (Amersham) with $^{32}$P labeled probes generated by random priming (Boehringer-Mannheim). When using the targeting ptDNA as a probe, in lines At-pGS31A-2 and At-pGS31A-16, the 3.82-kb transgenic fragment was the only fragment detected indicating that the wild-type ptDNA copies have been selectively diluted out during cell divisions on the selective medium. The same transgenic fragment also hybridized with the aadA probe (FIG. 1C).

Among the 19 spectinomcycin resistant lines 17 nuclear transformants were identified by a wild-type fragment on Southern blots when hybridizing with the targeting ptDNA probe. Note that the Southern blots used were optimized for the high-copy (10,000 per cell) leaf ptDNA and will not give a signal with a few nuclear aadA copies.

Spontaneous mutants are expected to have wild-type ptDNA targeting fragment on Southern blots and no PCR-amplifiable aadA gene. In the sample of 19 spectinomycin resistant lines, no such spontaneous mutant was found.

PCR Amplification of Inserted aadA Sequences

DNA was amplified according to standard protocols (1 min at 92° C., 1.5 min at 58 ° C., 1.5 min at 72° C., 30 cycles). Spectinomycin resistance being the result of aadA expression may be verified by PCR amplification of an 407 nucleotide internal segment using the following primers:
5'-GCTTGATGAAACAACGCGG-3'
5'-CCAAGCGATCTTCTTCTTGTCCAAG-3'.

Transplastomic Arabidopsis Plants

While the transplastomic Arabidopsis plants all flowered, none of them set seed after selfing, or after fertilization with pollen from wild-type plants. Included among these were 98 plants regenerated from the two lines in which spectinomycin resistance was due to plastid transformation, and 66 plants regenerated from 12 lines in which spectinomycin resistance was due to expression of aadA in the nuclear genome.

Conclusions and Implications

An important agricultural breakthrough, plastid transformation in the model species *Arabidopsis thaliana* is described in the instant invention. Based on the foregoing results, it has been found that a chimeric aadA gene, when inserted in the Arabidopsis ptDNA targeting cassette, was suitable to recover plastid transformants following biolistic delivery of the transforming DNA. However, the number of Arabidopsis plastid transformants was significantly lower, about one in 100, than anticipated based on the transformation of tobacco plastids which yields on average one transformant per bombarded sample (Svab and Maliga, 1993; Zoubenko et al., 1994). There may be multiple reasons for the relatively low transformation efficiency. Inherent species-specific differences, such as relatively inefficient homologous recombination system in Arabidopsis chloroplasts could be one obvious reason.

In tobacco vector pZS197, aadA is flanked by 1.56-kb and 1.29-kb of ptDNA, and yields—1 transformant per bombardment (Svab et al., 1993). In plasmid pRB15, also a tobacco vector, aadA is flanked by larger targeting segments, 1.56-kb and 3.6-kb of ptDNA, and yields approximately 5 plastid transformants per bombardment (Bock and Maliga, 1995). In Arabidopsis vector pGS31A aadA is flanked only by approximately 1-kb plastid targeting sequence on both sides. Therefore, the efficiency of plastid transformation in Arabidopsis may be significantly improved by increasing the size of the targeting ptDNA fragment.

In contrast to tobacco, in which most of the plants regenerated from leaves are fertile, it was surprising to find that none of the 164 regenerated Arabidopsis plants set seed. Lack of fertility, in part, may be due to the extensive polyploidy of leaf tissue as reported by Galbright et al., (1991) and Melaragno et al. (1993). An additional reason for lack of fertility may be the prolonged exposure of the cultures to 2,4 D (Van der Graaff and Hooykaas, 1996).

EXAMPLE II

Plastid Transformation in Arabidopsis Cotyledons by Selection for Kanamycin Resistance Plastid transformation has been obtained in *Arabidopsis thaliana* by selection for spectinomycin resistance in leaf cultures following bombardment with DNA-coated tungsten particles, as set forth in Example I. While plastid transformation has been successful, the regenerated plants were not fertile. These obstacles have been overcome by altering certain parameters of the transformation protocol.

The protocol developed and set forth in this Example has the following salient features: (1) Cotyledons obtained by germinating mature seed are used to advantage because of their ready availability, and the ease by which large quantities of sterile cotyledons are obtained from surface-sterilized seed. (2) The protocol has two distinct steps. The first step employing a high auxin medium to induce uniform cell division throughout the cotyledon (Stage I) and the second step including a high cytokinin medium to induce plant regeneration (Stages II and III). The protocol was designed to either minimize exposure to medium containing 2,4-D during tissue culture, or more preferably to eliminate such exposure completely. (3) Initial culturing of the cotyledon cells at a high density, i.e., 500–200 cotyledons/20 ml in liquid culture medium during the first 8 days (Stage I, II) proved essential for obtaining abundant plant regeneration later.

Figure 4:
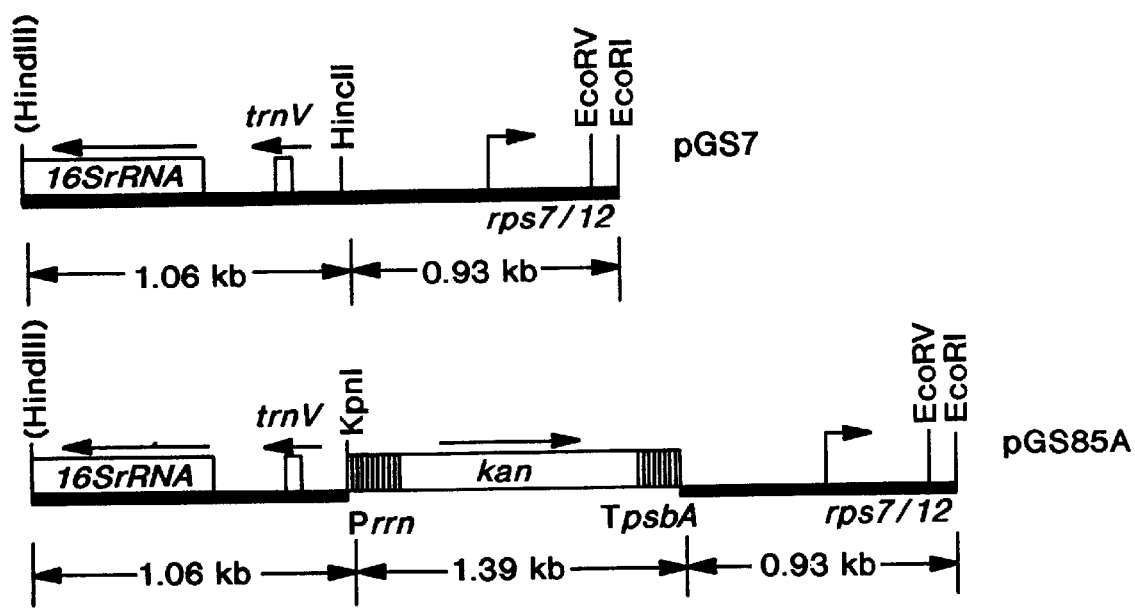
FIG. 4 is a map of the plastid targeting region of pGS7 and pGS85A plasmids. Note unique HincII cloning site in plasmid pGS7 and KpnI restriction site in plasmid pGS85, and chimeric kan kanamycin resistance gene. The plastid genes trnV, 16SrDNA and rps12/7 are described in Shinozaki et al., 1986. Site and direction of transcription initiation is indicated by horizontal arrow.

The protocol for plastid transformation in Arabidopsis utilizing cotyledons as target tissue and kanamycin-resistance as a selective marker was implemented as follows. The chimeric kan gene derives from plasmid pTNH7, a pUC118 derivative encoding neomycin phosphotransferase (NPTII), an enzyme which enzymatically inactivates the kanamycin antibiotic. The same chimeric kan gene in a tobacco targeting plasmid (plasmids pTNH32) was used for direct selection of plastid transformants in tobacco (Carrer et al. 1993) The construction of the kan gene was described in more detail in this same reference. Plasmid pGS85A was obtained by excising kan from pTNH7 as a SacI/PstI fragment, blunting, and cloning the fragment into the HincII site of plasmid pGS7 (FIG. 4). The kan gene in pGS85A, as aadA in plasmid pGS31A, is expressed in a Prrn/TpsbA cassette. However, the five N-terminal amino acids of the highly-expressed rbcl coding region were translationally fused with the neomycin phosphotransferase N-terminus. This translational fusion in tobacco lead to the accumulation of NPTII at 10× higher levels than from identical constructs without the rbcl N-terminal segment. The DNA sequence of pGS85A, including that of the chimeric kan gene, is set forth herein.

Initially, seed-set was tested in plants regenerated via the tissue culture protocol. Selection of kanamycin resistant clones after bombardment with DNA-coated tungsten was subsequently assessed. These improvements to the method are suitable for the generation of fertile, transformed Arabidopsis plants. The following material and protocols were utilized in practicing the methods of this Example II.

Seed Germination

Seeds of *Arabidopsis thaliana* ecotype RLD are surface sterilized using commercial bleach (5% sodium hypochlorite) for 5 minutes followed by a subsequent 5 minute treatment with 95% ethanol. A drop of Triton X-100 was added to the bleach to wet the surface of the seeds during the sterilization period. After sterilization, seeds were washed 5–6 times with sterile deionized water. Seeds were germinated on GM medium in 10 cm Petri dishes. See Table 2. The Petri dishes were incubated for 8 to 9 days in a Percival growth chamber at 23° C. under continous light.

TABLE 2

Composition of seed germination (GM) medium.

| Medium | Concentration (mg/L) |
|---|---|
| MS basal salts | 0.5 X |
| myo-inositol | 100 |
| Thiamine | 0.1 |
| Pyridoxine | 0.5 |
| Nicotinic acid | 0.5 |
| Glycine | 2.0 |
| Sucrose | 30 g/L |
| pH | 5.8 |

Reference: van der Graaff and Hooykaas, 1996.

Tissue Culture Media and Culture Conditions

Compositions of the tissue culture media used for Stages I, II and III of the selection protocol are listed in Tables 2 and 3. Stage I and Stage II liquid cultures were established by aseptically transferring at least 50 to 2000 cotyledons to a Petri dish (100 mm×20 mm), each dish containing approximately 20 ml of medium. The Petri dishes were incubated at 23° C. on a New Brunswick G10 gyrotory shaker at 60 rpm and illuminated for 16 hours with cool fluorescent light. In the Stage III protocol, cotyledons were incubated on agar-solidified (0.8% TC agar, JRH Biosciences) media at approximately 25–30 cotyledons per Petri dish (100 mm×20 mm) in 50 ml of media. The cultures were illuminated as described for Stages I and II.

Regenerated plants were directly transferred to GM medium in Magenta boxes with vented lids for gas exchange. Plants in the Magenta boxes were incubated in the culture room at 23° C.; and illuminated for 16 hours with cool fluorescent light. The plants flowered and set seeds in the boxes.

The methods described for Example I were modified to generate fertile Arabidopsis plants having transformed plastid genomes. Three distinct tissue culture stages were employed to obtain plastid transformation. Stage I: liquid culture, in high auxin medium to stimulate uniform cell division. Stage II: liquid culture, in high cytokinin medium to induce plant regeneration from the transformed cells. Stage III: culture on agar-solidified medium, containing high levels of cytokinins also to induce plant regeneration.

Figure 3:
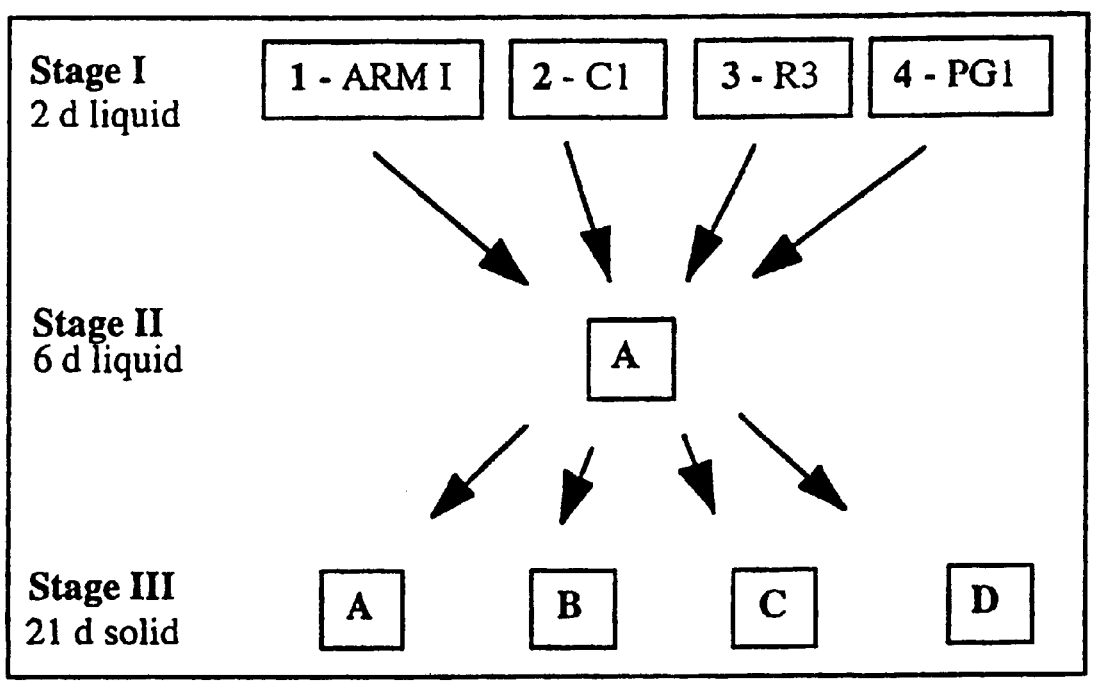
FIG. 3 is a schematic diagram of the different protocols used for obtaining fertile Arabidopsis plants from cotyledonary explants of *Arabidopsis thaliana* (RLD) having transformed plastids.

A schematic diagram of the strategy used to identify the best protocol for obtaining fertile plastid transformants is outlined in FIG. 3. To induce uniform cell division in liquid culture, four media, C1 (van der Graaff and Hooykaas, 1996), ARM I (Marton and Browse, 1991), R3 and PG1 (Feldmann and Marks, 1986; reported to induce callus and/or somatic embryogenesis in Arabidopsis) were utilized. Stage I treatment was kept short (2 days) to adopt to the usual timing of transferring the explants to a selective medium after bombardment, and to minimize the adverse effect of 2-4-D, if used at all. The composition of the Stage I tissue culture media utilized is set forth in Table 3 below.

TABLE 3

Composition of Stage I tissue culture media*.

| Media | ARM I | C1 | R3 | PG1 |
|---|---|---|---|---|
| Basal salts | MS | MS | MS | MS |
| Vitamins | ARM I | B5 | MS | B5 |

TABLE 3-continued

Composition of Stage I tissue culture media*.

| | | | | |
|---|---|---|---|---|
| 2,4-D | 0.15 | — | 0.5 | 2.2 |
| BAP | 0.6 | 0.2 | — | — |
| IAA | 3.0 | — | 5.0 | — |
| IPA | 0.3 | — | — | — |
| NAA | — | 1.0 | — | — |
| KIN | — | — | 0.3 | 0.05 |
| Sucrose | 30 g | 30 g | 30 g | 30 g |
| pH | 5.8 | 5.8 | 5.8 | 5.8 |

*All components are in mg/L.
References:
ARM1, Marton and Browse, 1991;
C1, van der Graaff and Hooykaas, 1996;
R3 and PG1, Feldmann and Marks (1986).

For Stage II culture, only one medium (A; Table 4) was used. This medium was efficient for inducing plant regeneration from immature cotyledons (Patton and Meinke, 1988). The cotyledons at Stage II were kept for a total of 6 additional days at high density in liquid culture.

For Stage III culture, the cotyledons were transferred to four types of agar-solidified regeneration media. These include the A medium developed for plant regeneration from immature embryos (Patton and Meinke, 1988); the B medium developed for plant regeneration from root explants (ARMII; Marton and Browse, 1991); the C medium that designed herein; and the D medium which is an embryo-induction medium for roots (ARMI; Marton and Browse, 1991) and leaf explants (Example I).

TABLE 4

Stage II and Stage III plant regeneration media.

| Media | A medium* | B medium* | C medium* | D medium* |
|---|---|---|---|---|
| Basal salts | MS | MS | MS | MS |
| Vitamins | B5 | B5 | B5 | B5 |
| NAA | 0.1 | — | 0.1 | — |
| IAA | — | 0.1 | — | 3.0 |
| BAP | 1.0 | — | 1.0 | 0.6 |
| 2iP | — | 4.0 | 2.0 | 0.3 |
| 2,4-D | — | — | — | 0.15 |
| Sucrose | 30 g | 30 g | 30 g | 30 g |
| Agar (TC) | 7 g | 7 g | 7 g | 7 g |
| pH | 5.8 | 5.8 | 5.8 | 5.8 |

*All components are in mg/L.
A medium is based on Patton and Meinke, 1988;
B medium is the same as ARMII in Marton and Bowse, 1991;
C medium developed herein, based on A and D media;
D medium is the same as ARMI embryo-induction medium in Marton and Browse, 1991.

Plant Regeneration and Testing of Fertility

Cotyledons remained green and slightly expanded in size during the first 2 days of culture at Stage I in all four media. After 2 days in callus/embryo induction medium, cotyledons for Stage II were transferred from all four media to the A liquid regeneration medium. Green callus started appearing after 3 days of culture in A medium and by the 7th day callus appeared all over the cotyledons. At this stage cultures were transferred to the semi-solid media of Stage III which promotes embryo/shoot growth. Calli derived from media 1 (ARM1) and 2 (C1) were green. Development of plantlets from these explants could be seen by 21 days of culture. Callus derived from media 3 (R3) and 4 (PG1) was also green but very compact. This is probably due to the high concentration of 2,4-D in the Stage I media. A few plantlets in these cultures appeared only after 30 days. Plants from all cultures were transferred to hormone free GM medium as soon as they were 5–10 mm in size.

The protocols diagrammed in FIG. 3 were evaluated at two levels: uniform induction of cell division and shoot regeneration from the cotyledons; and by production of viable seed on the regenerated plants. The results are summarized in Table 5. Based on the first criterion, the best combination was 2AC, that is C1 medium at Stage I and C medium at Stage III, these treatments resulted in prolific shoot regeneration which was observed on each of the explants. The second best combination was 1AC (35 out of 40 explants regenerating shoots), with ARM1 at Stage I and medium C at Stage III. Combinations with media 3 and 4 at Stage I performed very poorly, with only a very small fraction of cotyledons forming shoots.

As to formation of viable seed, with one exception each of the regenerated plants produced viable seed. See Table 5. Most importantly, no adverse effect on fertility was found in the two combinations (2AC and 1AC) in which shoot regeneration is prolific.

TABLE 5

Seed-set in Magenta boxes an *Arabidapsis thaliana* RLD plants regenerated via plastid transformation protocols schematically shown in FIG. 3.

| Media | Number of cotyledons cultured | Number of cotyledons with shoots | Number of plants in boxes | Number of with viable seed |
|---|---|---|---|---|
| 1AA | 40 | 20 | 8 | 8 |
| 1AB | 40 | 25 | 8 | 8 |
| 1AC | 40 | 35 | 8 | 8 |
| 1AD | 40 | — | — | — |
| 2AA | 40 | 25 | 12 | 12 |
| 2AB | 40 | 22 | 8 | 7 |
| 2AC | 40 | 40 | 16 | 16 |
| 2AD | 40 | 2 | — | — |
| 3AA | 40 | 12 | 4 | 4 |
| 3AB | 40 | 6 | 4 | 4 |
| 3AC | 40 | 20 | — | — |
| 3AD | 40 | 1 | — | — |
| 4AA | 40 | 1 | — | — |
| 4AB | 40 | 1 | — | — |
| 4AC | 40 | 4 | 4 | 4 |
| 4AD | 40 | 1 | — | 1 |

Selection of Plastid Transformants by Kanamycin Resistance

Expression of kan encoding neomycin phosphotransferase (NPTII) confers resistance to kanamycin when introduced into the Arabidopsis nucleus. Engineered forms of ksn have been extensively used to obtain nuclear transformants in Arabidopsis, see Valvekens et al., 1998. and Brassica, see Radke, et al. 1992. The kan gene has been converted into a plastid marker for the selection of plastid transformants in tobacco (Carrer et al., 1993). As set forth in Example I, Aradiposis plastid transformants have been obtained by selection for spectinomycin resistance conferred by aadA in the tobacco Prrn/TpsbA cassette. Prrn is a promoter derived from the plastid rRNA operon and TpsbA contains the plastid psbA gene 3' untranslated region required for the stabilization of chimeric plastid mRNAs (Svab and Maliga, 1993). A kanamycin resistance marker gene suitable for the selection of plastid transformants may be obtained by expressing kan in the Prrn/TpsbA cassette. A suitable kanamycin resistance plastid transformation vector from Arabidopsis and Brassica is the pGS85A vector which carries the chimeric kanamycin gene from plasmid pTNH32 (Carrer et al. 1993). The insertion site in pGS85A is the Hinc II site in the trnV/rps12/7 intergenic region. However, other intergenic regions in the plastid genome may be targeted, providing the introduced transgene does not interfere with the expression of the flanking plastid genes.

Plastid transformation may be carried out following the 1AC or 2AC tissue culture protocols outlined above. To prepare a suitable target tissue for transformation, cotyledons from 8–9 day old seedlings are cut from seedlings in liquid ARM1 and C1 media and cultured for two days as dictated by the 1AC and 2AC protocols (FIG. 3). After two days the cotyledons are transferred to filter paper (Whatman No. 4) on agar-solidified non-selective medium of identical composition. Approximately 50 to 70 cotyledons are required to cover a 3 cm$^2$ area. The cotyledons are then bombarded with plasmid pGS85A, a kanamycin resistance, transforming Arabidopsis vector. Plasmid preparation, coating of tungsten particles and bombardment should be carried out as described for tobacco (Maliga, 1995). For phenotypic expression, the cotyledons may be left in the same plates for two days. Subsequently, the cotyledons may be transferred to a selective liquid A medium containing 50 mg/L kanamycin sulfate and cultured for an additional seven days. After 7 days, cotyledons are transferred to a selective, agar-solidified C medium containing 50 mg/L kanamycin. In an alternative embodiment, selection may be carried out initially using kanamycin at 25 mg/ml. At later stages of culture, the kanamycin concentration is increased to 50 mg/ml. Callus growth from the transformed cells on the selective medium may be observed as early as one week. However, additional kanamycin-resistant clones may appear for several more weeks. Some of these are plastid transformants, while others acquire resistance to kanamycin due to the expression of the plastid kan gene in the nucleus (Carrer et al., 1993). The two classes of kanamycin-resistant clones can be readily distinguished DNA gel blot analysis and PCR analysis (as described in Example I). DNA was amplified according to standard protocols (1 min at 92° C., 1.5 min at 58° C., 1.5 min at 72° C., 30 cycles). Kanamycin resistance occurs as the result of neomycin phosphotransferase gene expression which may be verified by PCR amplification of a 548 nucleotide internal segment using the following primers:

5'-CCGACCTGTCCGGTGCCC-3'
5'-CACGACGAGATCCTCGCCG-3'.

EXAMPLE III

Plastid Transformation in *Brassica napus* Leaves by Selection for Resistance to Spectinomycin and Kanamycin Given their essentially identical genomes, plastid transformation vectors and expression cassettes developed for Arabidopsis can be used to advantage for plastid transformation and expression of foreign genes in Brassica species without modification.

Certain plastid expression signals derived from evolutionarily distant species function in Arabidopsis and Brassica plastids. This observation is supported by the results described in Example I demonstrating that the tobacco Prrn/TpsbA cassette can be used for expressing the selectable spectinomycin resistance gene (aadA) in Arabidopsis plastids. However, not every tobacco expression signal functions properly in Arabidopsis. Studies with a vector identical to PGS31A, except that the termination signal TpsbA, has been replaced with signal Trps16 has a dramatic effect on obtaining plastid transformants. This plasmid gene was obtained by inserting the Prrn/Trps16 cassette into targeting site in the pGS7 vector. See FIG. 4. Zero plastid transformants were obtained out of 416 samples bombarded with this plasmid. As mentioned above, when a Prrn/TpsbA cassette (cassettes described in Staub and Maliga, Plant Journal 6:547–553, 1994 and Svab and Maliga, 1993, the subject matter of which is incorporated herein by reference) was utilitized to transform Arabidopsis leaves, plastid transformants were obtained, 2 out of 210 samples bombarded.

Due to their taxonomic relatedness, Arabidopsis and Brassica species respond similarly in tissue culture to plant hormones or to antibiotics. As a result, plant regeneration from cultured cells and selection of transgenic lines by antibiotic resistance may be accomplished by essentially the same protocol. Both Arabidopsis and Brassica leaf or cotyledon explants respond to 500 mg/L spectinomycin with prolific callus growth in wild-type, non-transformed tissue on shoot regeneration medium, such as medium C described in Table 6. This response differs significantly in tobacco leaf tissue wherein exposure to 500 mg/ml of spectinomycin results in a severe inhibition of callus proliferation on shoot induction medium. Thus, tobacco plastid (and nuclear gene) transformants can be readily regenerated on a shoot induction medium containing spectinomycin at 500 mg/L (Svab and Maligam 1993). Unfortunately, rapid callus proliferation on spectinomycin-containing C shoot/embryo regeneration medium (see table 6) prevents the recovery of Arabidopsis and Brassica plastid transformants. Culture conditions must be improved to suppress rapid callus growth to facilitate the recovery of plastid transformants. Such conditions are outlined in Example I. While selection was feasible and plastid transformants were obtained using the methods of Example I, the transplastomic plants generated were not fertile. However, given the higher tolerance of Brassica to 2,4 D (Radke et al., 1992) the same protocol described in example I may be adapted for use in Brassica.

The data presented in Example II indicate that kanamycin selection is compatible with the regeneration protocols described. Accordingly, kanamycin is the favored antibiotic for the selection of plastid transformants in the Cruciferae taxonomic group.

Examples I and II disclose protocols for the regeneration of transgenic plants from Arabidopsis leaves and cotyledons. A protocol for the regeneration of transgenic plants in Brassica would involve a two-stage protocol (application of two different media) for leaves, and a three-stage protocol (application of three different media) for cotyledons. The three-stage protocol described for use in the plastid transformation of Arabidopsis cotyledons in Example II is suitable for use in Brassica. Accordingly only the methods for transforming Brassica leaf plastids in a two stage process will be described below Plastid Transformation in Brassica Utilizing Leaves as Target Tissue and Kanamycin Resistance as the Selective Marker Brassica Stage I culture results in the uniform induction of cell division in leaves or cotyledons. The objective of Stage II is regeneration of transgenic plants. A suitable Stage I medium for the induction of cell division would be the ARMI medium discussed in Examples I and II. Suitable Stage II regeneration media would be the B medium (ARMII in Marton and Browse, 1991), C medium (this study) and E medium (Pelletier et al. 1983) listed in Table 6.

TABLE 6

Stage II Brassica plant regeneration media*

| Media | B medium | C medium | E medium |
|---|---|---|---|
| Basal salts | MS | MS | MS |
| Vitamins | B5 | B5 | B5 |
| NAA | — | 0.1 | 1.0 |
| IAA | 0.1 | — | — |
| BAP | — | 1.0 | — |
| 2iP | 4.0 | 2.0 | 1.0 |
| GA3 | — | — | 0.02 |
| Sucrose | 30 g | 30 g | 30 g |
| Agar (TC) | 7 g | 7 g | 7 g |
| pH | 5.8 | 5.8 | 5.8 |

*All components are in mg/L.
B medium is the same as ARMII in Marton and Bowse, 1991;
C medium is this study;
E medium is the cruciferae For selection of plastid transformants, *Brassica napus* cv. Westar seeds should be surface sterilized, and germinated aseptically in Magenta boxes as described for Arabidopsis in Example II. After three to four weeks, the leaves are harvested, and directly placed a Whatman filter paper placed on agar-solidified non-selective Stage I medium. Following bombardment with DNA of the appropriate plastid transformation vector carrying a selectable kanamycin-resistance marker, as described in Example II, the plates are incubated for two days in the light (16 hours) at 25° C. After 2 days the leaves are incised with a stack of sterile razor blades, and transferred to the same Stage I medium supplemented with 50 mg/L of kanamycin sulfate. In an alternative embodiment, selection may be carried out initially using kanamycin at 25 mg/ml. At later stages of culture, the kanamycin concentration is increased to 50 mg/ml. After two weeks on the selective Stage I medium, the leaves are transferred to one of the Stage II media for plant regeneration. Kanamycin resistant clones are identified by their rapid growth and shoot regeneration on the selection medium. Kanamycin resistance may be due to plastid transformation or integration of the kanamycin marker gene into the nuclear genome. Plastid transformation is verified by PCR and DNA gel blot analysis in tissue samples taken from kanamycin-resistant calli and regenerating shoots. The regenerated shoots are then rooted and transferred to soil in the greenhouse following standard protocols.

REFERENCES

1. Bendich, A. J. (1987) Why do chloroplasts and mitochondria contain so many copies of their genome? Bioessays 6, 279–282.
2. Bock, R. and Maliga, P. (1995) In vivo testing of a tobacco plastid DNA segment for guide RNA function in psbL editing. Molec. Gen. Genet. 247, 439–443.
3. Carrer, H., Hockenberry, T N, Svab, Z., Maliga, P. (1993) Kanamycin resistance as a selectable marker for plastid transformation in tobacco. Molec. Gen. Genet. 241, 49–56.
4. Carrer, H., Maliga, P. (1995) Targeted insertion of foreign genes into the tobacco plastid genome without physical linkage to the selectable marker gene. Biotechnology 13, 791–794.
5. Czako, M., Wilson, J. and Marton. L. (1993) Sustained root culture for generation and vegetative propagation of transgenic *Arabidopsis thaliana*. Plant Cell Rep. 12, 603–606.
6. Fromm, H., Edelman, M., Aviv, D. and Galun, E. (1987) The molecular basis of basis of rDNA-dependent specti-nomycin resistance in Nicotiana chloroplasts. EMBO J., 6, 3233–3237.
7. Galbright, D. W., Harkins, K. R. and Knapp, S. (1991) Systemic endopolyploidy in *Arabidopsis thaliana*. Plant Physiol. 96, 985–989.
8. Goulds, T., Maliga, P. & Koop, H. U. (1993) Stable plastid transformation in PEG-teated protoplasts of *Nicotiana tabacum*. Bio/Technology, 11, 95–97
9. Hajdukiewicz, P., Svab, Z. and Maliga, P. (1994) The small, versatile pPZP family of Agrobacterium binary vectors for plant transformation. Plant. Mol. Biol. 25, 989–994.
10. Maliga, P. (1993) Towards plastid transformation in flowering plants. Trends Biotechnol., 11, 101–106.
11. Maliga, P. (1995) Biolistic transformation of tobacco cells with nuclear drug resistance genes. In Methods in Plant Molecular Biology—A Laboratory Manual, (Maliga, P., Klessig, D., Cashmore, A., Gruissem W. and Varner, J., eds.). Cold Spring Harbor: Cold Spring Harbor Laboratory Press, pp. 37–54.
12. Maliga, P., Carrer, H., Kanevski, I., Staub, J., Svab Z. (1993) Plastid engineering in land plants: a conservative genome is open to change. Phil. Trans. R. Soc. Lond. B 341, 449–454.
13. Marton, L. and Browse, J. (1991) Facile transformation of *Arabidopsis thaliana*. Plant Cell Rep. 10, 235–239.
14. McBride, K. E., Svab, Z., Schaaf, D. J., Hogan, P. S., Stalker, D. M., Maliga, P. (1995) Amplification of a chimeric Bacillus gene in chloroplasts leads to an extraordinary level of an insecticidal protein in tobacco. Biotechnology, 13, 362–365.
15. Melaragno, J. E., Mehrotra, B. and Coleman, A. W. (1993) Relationship between endopolyploidy and cell size in epidermal tissue of *Arabidopsis*. Plant Cell 5, 1661–1668.
16. Mettler, I. J. (1987) A simple and rapid method for minipreparation of DNA from tissue cultured plant cells. Plant Mol. Biol. Reporter 5, 346–349.
17. Meyerowitz, E. M. and Somerville, C. R. (1994) Arabidopsis. Cold Spring Harbor: Cold Spring Harbor Laboratory Press.
18. Murashige, T. and Skoog, F. (1962) A revised medium for rapid growth and bioassays with tobacco tissue culture. Physiol. Plant., 15, 493–497.
19. O'Neill, C, Horvath, G. V., Horvath, E., Dix, P. J. and Medgyesy, P. (1993) Chloroplast transformation in plants: polyethylene glycol (PEG) treatment of protoplasts is an alternative to biolistic delivery systems. Plant J., 3, 729–738.
20. Palmer, J. D. (1991) Plastid chromosomes: structure and evolution. In The Molecular Biology of Plastids, Cell Culture and Somatic Cell Genetics of Plants, vol. 7A (L. Bogorad, L. and Vasil I. K. eds.). San Diego: Academic Press, pp. 5–53.
21. Palmer, J. D., Downie, S. R., Nugent, J. M., Brandt, P., Unseld, M., Klein, M., Brennicke, A., Schuster, W. and Borner, T. (1994) Chloroplast and mitochondrial DNAs of *Arabidopsis thaliana:* Conventional genomes in an unconventional plant. In Arabidopsis, (Meyerowitz, E. M. and Somerville, C. R., eds.) Cold Spring Harbor: Cold Spring Harbor Laboratory Press, pp. 37–62.
22. Shinozaki, K., Ohme, M., Tanaka, M., Wakasugi, T., Hayashida, N., Matsubayashi, T., Zaita, N., Chunwongse, J., Obokata, J., Yamaguchi-Shinozaki, K., Ohto, C., Torazawa, K., Meng, B. Y., Sugita, M., Deno, H., Kamoyashira, T., Yamada, K., Kusuda, J., Takawa, F., Kato, A., Tohdoh, N., Shimada, H. and Suguira, M. (1986)

The complete nucleotide sequence of the tobacco chloroplast genome: its gene organization and expression. EMBO J., 5, 2043–2049.
23. Staub, J. & Maliga, P. (1992) Long regions of homologous DNA are incorporated into the tobacco plastid genome by transformation. Plant Cell 4, 39–45.
24. Svab, Z. and Maliga, P. (1991) Mutation proximal to the tRNA binding region of the Nicotiana plastid 16S rRNA confers resistance to spectinomycin. Molec. Gen. Genet. 228, 316–319
25. Svab, Z. and Maliga, P. (1993) High-frequency plastid transformation in tobacco by selection for a chimeric aadA gene. Proc. Natl. Acad. Sci. USA, 90, 913–917.
26. Svab, Z. and Maliga, P. (1993) High-frequency plastid transformation in tobacco by selection for a chimeric aadA gene. Proc. Natl. Acad. Sci. USA, 90, 913–917.
27. Svab, Z., Hajdukiewicz, P. and Maliga, P. (1990a) Stable transformation of plastids in higher plants. Proc. Natl. Acad. Sci. USA, 87, 8526–8530
28. Svab, Z., Harper, E. C., Jones, J. D. G. and Maliga, P. (1990b) Aminoglycoside-3"-adenyltransferase confers resistance to spectinomycin and streptomycin in Nicotiana tabacum. Plant Mol. Biol. 14, 197–205.
29. Valvekens, D., Van Motagu, M. and Van Lijsebettens, M. (1988) Agrobacterium tumefaciens-mediated transformation of Arabidopsis thaliana root explants using kanamycin selection. Proc. Natl. Acad. Sci. USA 85, 5536–5540.
30. Zoubenko, O. V., Allison, L. A., Svab, Z. and Maliga, P. (1994) Efficient targeting of foreign genes into the tobacco plastid genome. Nucleic Acids Res., 22, 3819–3824.
31. Feldmann, K. A. and Marks, M. D. (1986) Rapid and efficient regeneration of plants from explants of Arabidopsis thaliana. Plant Sci. 47: 63–69.
32. Lloyd, A. M., Barnason, A. R., Rogers, S. G., Byrne,, M. C., Fraley, R. T., Horsch, R. B. (1986) Science 234:464–466.
33. Patton, D. A. and Meinke, D. W. (1988) High-frequency plant regeneration from cultured cotyledons of Arabidopsis thaliana. Plant Cell Reports 7:233–237.
34. Van der Graaff, E. and Hooykaas, P. J. J. (1996) Improvements in the transformation of Arabidopsis thaliana. C24 leaf-discs by Agrobacterium tumefaciens Plant Cell Rep. 15: 572–577.
35. Pelletier, G., Primard, C., Vedel, F., Chetrit, P. Remy, R. Rousselle, R. and Renard M. (1983) Intergeneric cytoplasmic hybridization in cruciferae by protoplast fusion. Mol. Gen. Genet. 191:244–250.
36. Radke, S. E., Turner, J. C., and Facciotti D. (1992) Transformation and regereation of Brassica rapa using Agrobacterium tumefaciens. Plant Cell Reports 11:499–505.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A method for obtaining transplastomic *Arabidopsis* plants, comprising:
   a) culturing *Arabidopsis* plant cells from said *Arabidopsis* plant in a high auxin containing medium that stimulates uniform cell division;
   b) transferring said plant cells to filter paper on agar-solidified medium;
   c) delivering to a plastid genome within said plant cells, a transforming DNA molecule, said transforming DNA molecule having;
      i) a plurality of targeting segments comprising plastid DNA sequences from said plastid genome to be transformed, said targeting segments facilitating homologous recombination of said transforming DNA into said plastid genome;
      ii) 5' and 3' regulatory sequences derived from plastid DNA operably linked to a selectable marker gene disposed within said targeting segment, said regulatory sequences facilitating expression of the selectable marker gene and stability of mRNA encoded therefrom, said selectable marker gene conferring resistance to a selection agent in said plant cells;
      iii) 5' and 3' regulatory sequences derived from plastid DNA operably linked to coding sequences comprising a foreign gene of interest thereby facilitating expression of the foreign gene of interest and stability of mRNA encoded therefrom; and
      iv) at least one cloning site for insertion of said foreign gene of interest adjacent to said selectable marker gene, said insertion not interfering with said conferring of said selectable phenotype and function of flanking plastid genes;
   d) transferring cells transformed as in step (c) to an agar-solidified high cytokinin containing culture medium at high density for a predetermined time period; said culture medium containing an agent that promotes plant regeneration;
   e) transferring said cells treated as in step (d) to an agar-solidified culture medium containing said regeneration promoting agent and said selection agent, said transformed cells being rendered resistant to said selection agent by expression of said selectable maker gene; and
   f) selecting for cells having transformed plastid genomes and inducing plant regeneration therefrom.

2. A method as claimed in claim 1, wherein said transforming DNA is delivered by a method selected from the group consisting of biolistic bombardment of said cells with DNA-coated particles, CaPO$_4$ mediated transfection, electroporation, and polyethylene glycol mediated DNA uptake.

3. A method claimed as in claim 1, wherein said plant cells are selected from the group consisting of cotyledon cells, leaf cells, hypocotyls and root cells.

4. A method as claimed in claim 1, wherein said selectable marker gene and said foreign gene of interest constitute a monocistronic expression unit.

5. A method as claimed in claim 1, wherein said selectable marker gene and said foreign gene of interest constitute a polycistronic expression unit.

6. A method as claimed in claim 1, wherein said plastids are chloroplasts.

7. A method as claimed in claim 1, wherein said antibiotic is selected from the group consisting of kanamycin, spectinomycin, and streptomycin.

8. A method as claimed in claim 1, wherein said agent promoting uniform cell division is selected from the group consisting of NAA, IAA, and 2,4-D.

9. A method as claimed in claim 1, wherein said regeneration promoting agent is selected from the group consisting of BAP, 2iP, IPA and KIN.

10. A method as claimed in claim 1, wherein said transforming DNA is cloned within vector pGS31A.

11. A method as claimed in claim 1, wherein said transforming DNA is cloned within vector pGS85A.

12. A method as claimed in claim 1, wherein said transforming DNA is cloned within vector PGS7.

13. A method as claimed in claim 1, wherein said plant is *Arabidopsis thaliana*.

* * * * *

SEQUENCE LISTING

<160> NUMBER OF SEQ ID NOS: 7

<210> SEQ ID NO 1
<211> LENGTH: 19
<212> TYPE: DNA
<213> ORGANISM: Artificial Sequence
<220> FEATURE:
<223> OTHER INFORMATION: Sequence Source:/note="synthetic sequence"

<400> SEQUENCE: 1
gcttgatgaa acaacgcgg                                                        19

<210> SEQ ID NO 2
<211> LENGTH: 25
<212> TYPE: DNA
<213> ORGANISM: Artificial Sequence
<220> FEATURE:
<223> OTHER INFORMATION: Sequence source:/note="synthetic sequence"

<400> SEQUENCE: 2
ccaagcgatc ttcttcttgt ccaag                                                 25

<210> SEQ ID NO 3
<211> LENGTH: 18
<212> TYPE: DNA
<213> ORGANISM: Artificial Sequence
<220> FEATURE:
<223> OTHER INFORMATION: Sequence source:/note="synthetic sequence"

<400> SEQUENCE: 3
ccgacctgtc cggtgccc                                                         18

<210> SEQ ID NO 4

```
<211> LENGTH: 19
<212> TYPE: DNA
<213> ORGANISM: Artificial Sequence
<220> FEATURE:
<223> OTHER INFORMATION: Sequence source:/note="synthetic sequence"

<400> SEQUENCE: 4
cacgacgaga tcctcgccg                                                    19

<210> SEQ ID NO 5
<211> LENGTH: 1993
<212> TYPE: DNA
<213> ORGANISM: Arabidopsis thaliana
<220> FEATURE:
<221> NAME/KEY: unsure
<222> LOCATION: (483)...(483)
<223> OTHER INFORMATION: The residue at position 483 may be A, T, C or
      G.
<221> NAME/KEY: unsure
<222> LOCATION: (506)...(506)
<223> OTHER INFORMATION: The residue at position 506 may be A, T, C or
      G.
<221> NAME/KEY: unsure
<222> LOCATION: (1880)...(1880)
<223> OTHER INFORMATION: The residue at position 1880 may be A, T, C or
      G.

<400> SEQUENCE: 5
aagcttggta gtttccaccg cctgtccagg gttgagccct gggatttgac ggcggactta        60
aaaagccacc tacagacgct ttacgcccaa tcattccgga taacgcttgc atcctctgta       120
ttaccgcggc tgctggcaca gagttagccg atgcttattc cccagatacc gtcattgctt       180
cttctctggg aaaagaagtt caggacccgt aggccttcta cctccacgcg gcattgctcc       240
gtcaggcttt cgcccattgc ggaaaattcc ccactgctgc ctcccgtagg agtctgggcc       300
gtgtctcagt cccagtgtgg ctgatcatcc tctcggacca gctactgatc atcgccttgg       360
taagctattg cctcaccaac tagctaatca gacgcgagcc cctcctcggg cggattcctc       420
cttttgctcc tcagctacgg ggtattagca gccgtttcca gctgttgttc ccctcccaag       480
ggnaggttct tacgcgttac tcaccngtcc gccactgaa acaccacttc ccgtccgact        540
tgcatgtgtt aagcatgccg ccagcgttca tcctgagcca ggatcgaact ctccatgaga       600
ttcatagttg cattacttat agcttccttc ttcgtagaca aagctgattc ggaattgtct       660
ttcattccaa gtcataactt gtatccatgc gcttcatatt cgcatggagt tcgctcccag       720
aaatatagct accctaccc cctcacgtca atcccacgag cctcttatcc attcttattc        780
gatcacagcg agggagcaag tcaaaataga aaaactcaca ttcattgggt ttagggataa       840
tcaggctcga actgatgact tccaccacgt caaggtgaca ctctaccgct gagttatatc       900
ccttccccca tcaagaaata gaactgacta atcctaagtc aaagggtcga gaaactcaag       960
gccactattc ttgaacaact tggattggag ccgggctttc ctttcgcact ttatacgggt      1020
atgaaatgaa aataatggaa aaagttggat tcaattgtca actactccta tcggaaatag      1080
gattgactac ggattcgagc catagcacat ggtttcataa aaccgtacga ttctcccgat      1140
ctaaatcaag ccggttttac atgaagaaga tttgactcgg catgttctat tcgatacggg      1200
taggagaaac ggtattcttt tcttaaactt caaaaaatag agaataaga accaagtcaa       1260 gatgatacgg attaatcctt tattcttgcg ccaaagatct tcctattcca aggaactgga      1320
gttacatctc ttttccattt ccattcaaga gttcttatgt gtttccacgc cccttttaaga     1380 ccccgaaaaa tcgacaaatt ccctttttctt aggaccacat gcgagataac gaaaaaaaaa    1440
```

```
aagagagaat ggtaacccca cgattaacta tttatttat gaatttcata gtaatagaaa    1500
tacatgtcct accgaaacag aatttgtaac ttgctatcct atcatcttgc ctagcaggca    1560
aagatttcac tccgcgaaaa agatgattca ttcggatcaa catgaaagcc caactacatt    1620
gccagaattt atatattgga aagaggttta cctccttgct tctatggtac aatcctcttc    1680
ccgcggagcc tcctttcttc tcggtccgca gagacaaaat gtaggactgg tgccaacagt    1740
taatcacgga agaaaggact cactgcgcca agatcactaa ctaatctaat agaatagaaa    1800
atcctaatat aatagaaaag aaaagaactg tcttttctga tacttatgta tactttcccc    1860
ggttccgttg ctactgcggn tttacgcaat tgatcggatc atctagatat cccttcaaca    1920
caacataggt cgtcgaaagg atctcggaga cccgccaaag cacgaaagcc agaatctttc    1980
agaaaatgaa ttc                                                      1993

<210> SEQ ID NO 6
<211> LENGTH: 1143
<212> TYPE: DNA
<213> ORGANISM: Nicotiana tabacum

<400> SEQUENCE: 6
catgaataaa tgcaagaaaa taacctctcc ttctttttct ataatgtaaa caaaaaagtc      60
tatgtaagta aatactagt aaataaataa aagaaaaaa agaaaggagc aatagcaccc      120
tcttgataga acaagaaaat gattattgct ccttctttt caaaacctcc tatagactag      180
gccaggatcg ctctagctag acattatttg ccgactacct tggtgatctc gcctttcacg      240
tagtggacaa attcttccaa ctgatctgcg cgcgaggcca agcgatcttc ttcttgtcca      300
agataagcct gtctagcttc aagtatgacg ggctgatact gggccggcag gcgctccatt      360
gcccagtcgg cagcgacatc cttcggcgcg attttgccgg ttactgcgct gtaccaaatg      420
cgggacaacg taagcactac atttcgctca tcgccagccc agtcgggcgg cgagttccat      480
agcgttaagg tttcatttag cgcctcaaat agatcctgtt caagaaccgg atcaaagagt      540
tcctccgccg ctgacctac caaggcaacg ctatgttctc ttgcttttgt cagcaagata      600
gccagatcaa tgtcgatcgt ggctggctcg aagatacctg caagaatgtc attgcgctgc      660
cattctccaa attgcagttc gcgcttagct ggataacgcc acggaatgat gtcgtcgtgc      720
acaacaatgg tgacttctac agcgcggaga atctcgctct ctccagggga agccgaagtt      780
tccaaaaggt cgttgatcaa agctcgccgc gttgtttcat caagccttac ggtcaccgta      840
accagcaaat caatatcact gtgtggcttc aggccgccat ccactgcgga gccgtacaaa      900
tgtacggcca gcaacgtcgg ttcgagatgg cgctcgatga cgccaactac ctctgatagt      960
tgagtcgata cttcggcgac caccgcttct gccataaatc cctccctaca actgtatcca     1020
agcgcttcgt attcgcccgg agttcgctcc cagaaatata gccatccctg cccccctcacg    1080 tcaatcccac gagcctctta tccattctca ttgaacgacg gcggggagc tttgggtacc      1140 gag                                                                  1143

<210> SEQ ID NO 7
<211> LENGTH: 1417
<212> TYPE: DNA
<213> ORGANISM: Artificial Sequence
<220> FEATURE:
<223> OTHER INFORMATION: Sequence source:/note="synthetic construct"

<400> SEQUENCE: 7
gaattcgagc tcggtaccca aagctccccc gccgtcgttc aatgagaatg gataagaggc      60
```

```
                                    -continued tcgtgggatt gacgtgaggg ggcagggatg gctatatttc tgggagcgaa ctccgggcga      120
atacgaagcg cttggataca gttgtaggga gggatttatg tcaccacaaa cagaggggat      180
tgaacaagat ggattgcacg caggttctcc ggccgcttgg gtggagaggc tattcggcta      240
tgactgggca caacagacaa tcggctgctc tgatgccgcc gtgttccggc tgtcagcgca      300
ggggcgcccg gttcttttg tcaagaccga cctgtccggt gccctgaatg aactccagga       360
cgaggcagcg cggctatcgt ggctggccac gacgggcgtt ccttgcgcag ctgtgctcga      420
cgttgtcact gaagcgggaa gggactggct gctattgggc gaagtgccgg ggcaggatct      480
cctgtcatct caccttgctc ctgccgagaa agtatccatc atggctgatg caatgcggcg      540
gctgcatacg cttgatccgg ctacctgccc attcgaccac caagcgaaac atcgcatcga      600
gcgagcacgt actcggatgg aagccggtct tgtcgatcag gatgatctgg acgaagagca      660 tcagggctc gcgccagccg aactgttcgc caggctcaag gcgcgcatgc ccgacggcga       720
ggatctcgtc gtgacacatg gcgatgcctg cttgccgaat atcatggtgg aaaatggccg      780
cttttctgga ttcatcgact gtggccggct gggtgtggcg gaccgctatc aggacatagc      840
gttggctacc cgtgatattg ctgaagagct tggcggcgaa tgggctgacc gcttcctcgt      900
gctttacggt atcgccgctc ccgattcgca gcgcatcgcc ttctatcgcc ttcttgacga      960
gttcttctga gcgggactct ggggttcgga tcgatcctct agagcgatcc tggcctagtc     1020
tataggaggt tttgaaaaga aaggagcaat aatcattttc ttgttctatc aagagggtgc     1080
tattgctcct ttcttttttt cttttatt atttactagt attttactta catagacttt      1140
tttgtttaca ttatagaaaa agaaggagag gttattttct tgcatttatt catgattgag     1200
tattctattt tgattttgta tttgtttaaa ttgtgaaata gaacttgttt ctcttcttgc     1260
taatgttact atatctttt gatttttttt ttccaaaaaa aaaatcaaat tttgacttct     1320
tcttatctct tatctttgaa tatctcttat ctttgaaata ataatatcat tgaaataaga     1380
aagaagagct atattcgacc tgcaggcatg caagctt                              1417
```